United States Patent
Nagle

(10) Patent No.: US 12,161,609 B2
(45) Date of Patent: Dec. 10, 2024

(54) COMPOSITION AND METHOD FOR TREATING AUTISM SPECTRUM DISORDER (ASD) SYMPTOMS OF PARANOIA WITH SELF ISOLATION AND/OR AGGRESSION

(71) Applicant: John Nagle, Sylmar, CA (US)

(72) Inventor: John Nagle, Sylmar, CA (US)

(*) Notice: Subject to any disclaimer, the term of this patent is extended or adjusted under 35 U.S.C. 154(b) by 0 days.

(21) Appl. No.: 17/359,272

(22) Filed: Jun. 25, 2021

(65) Prior Publication Data

US 2022/0409556 A1 Dec. 29, 2022

(51) Int. Cl.
| | | |
|---|---|---|
| *A61K 31/137* | (2006.01) | |
| *A61K 31/165* | (2006.01) | |
| *A61K 31/55* | (2006.01) | |
| *A61P 25/18* | (2006.01) | |

(52) U.S. Cl.
CPC .......... *A61K 31/137* (2013.01); *A61K 31/165* (2013.01); *A61K 31/55* (2013.01); *A61P 25/18* (2018.01)

(58) Field of Classification Search
CPC .... A61K 31/137; A61K 31/165; A61K 31/55; A61P 25/18
See application file for complete search history.

(56) References Cited

U.S. PATENT DOCUMENTS

2007/0038264 A1* 2/2007 Jaax .................. A61N 1/36082
607/45

OTHER PUBLICATIONS

Coleman, "Rating of the Effectiveness of 26 Psychiatric and Seizure Medications for Autism Spectrum Disorder: Results of a National Survey", Journal of Child and Adolescent Psychopharmacology, vol. 29, No. 2, 2019, pp. 107-123.*
Novotny, Sherie; Oxcarbazepine Versus Placebo in Childhood Autism; U.S. National Library of Medicine, ClinicalTrials.gov; May 1, 2007; https://clinicaltrials.gov/ct2/show/results/NCT00467753?view=results.
Reddihough, Dinah et al.; A Randomized Placebo-Controlled Trial to Determine if Fluoxetine is Effective for Improving Autistic Behaviors; Journal of Paediatrics and Child Health; May 1, 2019; vol. 55, Issue S2; https://onlinelibrary.wiley.com/doi/10.1111/jpc.14466_2.
Ho, Beng-Choon et al.; Long Term Antipsychotic Treatment and Brain Volumes; Arch Gen Psychiatry; Feb. 2011; vol. 68, No. 2; https://ja1mmctwork.com/.
Leclerc, Sheena et al.; Pharmacological Therapies for Autism Spectrum Disorder: A Review; P&T Journal, Jun. 2015, vol. 40(6), pp. 389-397; https://www.ncbi.nlm.nih.gov/pmc/articles/PMC4450669/.
Lucchelli, Juan Pabloe et al.; Low-Dose Fluoxetine in Four Children with Autistic Spectrum Disorder Improves Self-Injurious Behavior, ADHD-Like Symptoms, and Irritability; Case Reports in Psychiatry; May 30, 2018; vol. 2018, Article ID 6278501; htlps://doi.org/ 10.1155/2018/6278501.
Uchida, Hiroyuki et al.; Dosing of antipsychotics in schizophrenia across the life-spectrum; Prog Neuropsychopharmacol Biol Psychiatry; Aug. 31, 2009; vol. 31;33(6), pp. 917-920; https:1/pubmed.n cbl.nlm.nih.gov/19426777/.
National Alliance on Mental Illness; Haloperidol (Haldol); The College of Psychiatric and Neurological Pharmacists; Feb. 2020; https://www.nami.org/About-Mental-Illness/Treatments/Mental-Health-Medications/Types-of-Medication/Haloperidol-(Haldol).
Strange, Brandon C; Once-daily treatment of ADHD with guanfacine: patient implication; Neuropsychiatric Disease and Treatment; 2008; vol. 4(3), pp. 499-506; Dove Medical Press Limited.
Williams, Katrina et al.; Selective serotonin reuptake inhibitors (SSRIs) for autism spectrum disorders (ASD) (Review); Cochrane Database of Systematic Reviews 2013, Aug. 2013; Issue 8, Art. No.: CD004677; The Cochrane Collaboration.

* cited by examiner

*Primary Examiner* — Sahar Javanmard
(74) *Attorney, Agent, or Firm* — Trojan Law Offices

(57) ABSTRACT

Autism (ASD) symptoms of aggression-toward others or self, and paranoia with social isolation, are presently treated with antipsychotic medications such as haloperidol, Thorazine, and newer generation antipsychotics risperidone and aripiprazole (latter two are the only FDA approved drugs for treating autism irritability/aggression). But these antipsychotics including the newer generation, after a two or more years of use, often lead to irreversible tardive dyskinesia, other dystonias, loss of effectiveness, and brain volume loss. The present invention overcomes the irreversible tardive dyskinesia and dystonias and loss of effectiveness with long term-use of antipsychotics, by replacing the antipsychotic completely with a three (3) drug novel composition consisting of fluoxetine or sertraline with guanfacine and oxcarbazepine. This novel composition markedly reduces aggression and paranoia/social isolation in ASD adults and adolescents without concomitant antipsychotic use that often causes irreversible tardive dyskinesia, eventual tachyphylaxis, or brain volume loss from antipsychotic long-term use.

18 Claims, No Drawings

COMPOSITION AND METHOD FOR TREATING AUTISM SPECTRUM DISORDER (ASD) SYMPTOMS OF PARANOIA WITH SELF ISOLATION AND/OR AGGRESSION

FIELD OF THE INVENTION

The present invention relates generally to finding a solution for replacing antipsychotic medications for treating Autism Spectrum Disorder (ASD) aggression and paranoia/social isolation with a drug composition that will not lead to irreversible tardive dyskinesia/dystonias and tachyphylaxis (loss of effectiveness) to treat aggression and/or paranoia/social isolation.

BACKGROUND OF THE INVENTION

ASD symptoms of aggression-toward others or self, and paranoia with social isolation, are presently treated with older antipsychotic medications such as haloperidol, Thorazine, and newer generation antipsychotics risperidone and aripiprazole. Risperidone and aripiprazole are the only currently FDA approved drugs for treating autism irritability and aggression. However, all of the older and newer generation of antipsychotics often, after a few years of use, lead to irreversible tardive dyskinesia or other dystonias. Long term use also leads to tachyphylaxis/loss of effectiveness. See, Dosing of antipsychotics in schizophrenia across the life spectrum, H. Uchida, D. Mamo, Progress in Neuro-Pharmacology and Biological Psychiatry, Aug. 2009 V. 33 (6) p.917-920. The high risk of dystonias such as tardive dyskinesia and of tachyphylaxis from long term use of antipsychotics is well reported,. See, "Haloperidol", NAMI (Arl., VA, Nat'l Alliance Mental Health webpage, Feb 2020, p.3) College of Psychiatric & Neurologic Pharmacists. The high risk of brain volume loss is also well reported with long term use of antipsychotics. Drs. Beng-Choon Ho and Nancy Andreasen, et al. Arch Gen. Psychiatry, Feb 2011, 68(2) p. 128-137. Currently, the standard psychiatric treatment for aggressive or paranoid ASD adolescents and adults is to use new generation antipsychotic such as risperidone or aripiprazole and add on to that treatment with other drugs to treat other symptoms, e.g., fluoxetine or sertraline for depression or anxiety.

The solution found in the present invention is the treatment of ASD aggression toward others or self and paranoia/social isolation with a novel composition comprising a combination of fluoxetine or sertraline with guanfacine and oxcarbazepine. None of these three drugs has been taught to be effective to treat autism aggression toward others or self-injury or paranoia with social isolation. Rather it is taught that each is not indicated for treating ASD without an antipsychotic medication or are ineffective for aggression and paranoia social isolation behaviors. The invented novel three drug composition overcomes the high risk of long term use toxic development of dystonias and loss of effectiveness/tachyphylaxis and also avoids the weight gain very often seen with long term use of the newer generation of antipsychotic in ASD patients. Because fluoxetine and sertraline mediate their actions as a serotonin reuptake inhibitor with the same active metabolite, both have been found to be effective in the composition combination. Because selective serotonin reuptake inhibitors (SSRIs) have the same pharmacologic pharmacodynamic effect on serotonin receptors, other SSRIs can be substituted for fluoxetine and sertraline in the present invention in combination with guanfacine and oxcarbazepine as of the composition for treating ASD aggression with paranoia/self-isolation.

In relation to treating with the fluoxetine, it includes fluoxetine hydrocholoride the standard formulation and the enteric coated slow-release formulation. In relation to sertraline, it includes sertraline hydrocholoride the standard formulation and the slow-release enteric formulation, and guanfacine includes guanfacine hydrochloride the standard formulation and its enteric coated slow-release formulation. In relation to oxcarbazepine, the oral suspension may be substituted for pills.

DESCRIPTION OF RELATED PRIOR ART

Haloperidol, thorazine and the new generation FDA approved risperidone and aripiprazole are presently the mainstay medical treatment for aggression toward others or self-injury and/or paranoia social isolation, seen in moderate to severe autism. S. LeClerk and D. Easley, Pharmacy & Therapeutics 2015 June; 40(6): 389-397. Currently, the standard psychiatric treatment for aggression or paranoia in ASD adolescents and adults is to use a new generation antipsychotic such as risperidone or aripiprazole.

The use of fluoxetine or sertraline or other serotonin reuptake inhibitors (SSRIs) (used to treat depression in children and adults) are taught as not effective or useful to treat ASD aggression or paranoia/self-isolation, but may be useful to treat obsessive compulsive disorder symptoms or depression (but they may have a side effect of seizures in some ASD subjects). K. Williams, A. Brignel, M. Randall. N. Silove. P. Hazzell, "Selective serotonin reuptake inhibitors (SSRIs) for autism spectrum disorders (ASD)(Review) p.2 "Summary". Cochrane Library (Publ. John Wiley & Sons) 2013, Issue 8. Fluoxetine is taught as not recommended to treat autism core behaviors. J. Pediatrics& Child Health V.55, Issue S2 D. Reddinghough, et al. May 2019, "A Randomized Placebo-Controlled Trial To Determine If Fluoxetine Is Effective For Improving Autistic Behaviors."

Guanfacine is used to treat hyperactivity/impulsivity in ADHD and comorbid ASD/ADHD, off label, but is not used by itself without an antipsychotic to treat aggression or paranoia in ASD patients. B. Strange, Neuropsychiatric Disease and Treatment, 2008 Jun. 4(3) 499-506, "Once-daily treatment of ADHD with guanfacine: patient implications."

Nor has oxcarbazepine, an anti-epileptic, been taught to be beneficial for treatment of ASD patients showing aggression or injury to self or paranoia or social isolation behavior, but it has been shown in autistic patients to have so many adverse effects in autistic subjects that they drop out of the study (cessation of use of anti-psychotics leads to "irritability" not overcome by oxcarbazepine, alone). See report of trial of" oxcarbazepine vs. placebo" (2011 to 2021) NCT 00467753, "Oxcarbazepine v. Placebo in Childhood Autism", S. Novotry, M. D. Rutgers State U. N.J., Clinical Trials.gov., NIH Nat'l Lib. Med.

SUMMARY OF THE INVENTION

A combination of three psychotropic medications, currently marketed as safe drugs for other indications (but not indicated or used or taught as helpful or able to treat autism aggression and/or paranoia) has in the present invention been found to be effective when used in combination to control self-injury, aggression and paranoia/social isolation behavior in autistic adolescents and adults, without dystonic side effects developing over long-term use. When the subjects were previously treated with risperidone or aripiprazole for aggression, self-injury and/or aggression toward others and/or paranoia they developed tardive dyskinesia after at two years use and tachyphylactic loss of effectiveness. After being taken off the antipsychotics risperidone and/or aripiprazole and put on the novel composition of three combined medications of SSRI (fluoxetine and/or sertraline) with guanfacine and oxcarbazepine, the ASD subjects' aggression and social isolation/paranoia was markedly alleviated as reported by parents, teachers and health care professionals. The novel combination used to treat these autistic adolescents and adults was fluoxetine or sertraline combined with oxcarbazepine and guanfacine. The preferred dosing is twice per day—first in the morning before breakfast and then before dinner.

DETAILED DESCRIPTION OF THE INVENTION

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another elements as illustrated in the FIGURES. It will be understood that relative terms are intended to encompass different orientations of the device in addition to the orientation depicted in the FIGURES.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

The present invention relates to a novel three drug composition for treating aggression and/or paranoia in autistic adolescents and adults employing three (3) compounds using safe and typical doses of each drug dosed together in the morning and evening.

The three compounds that make up the novel three drug composition are a selective serotonin reuptake inhibitor (SSRI) dosed with oxcarbazepine and guanfacine. The SSRI may be fluoxetine and/or sertraline. The novel three drug composition has a pharmacologically effective dose of the SSRI dosed with a pharmacologically effective does of oxcarbazepine and a pharmacologically effective dose of guanfacine. When fluoxetine is used as the SSRI in the novel composition, the pharmacologically effective dose for fluoxetine is 10 mg and 30 mg per dose. In these embodiments, the preferred dosage range for fluoxetine is 10 mg to 20 mg per dose. When sertraline is the SSRI in the novel composition, the pharmacologically effective dose for sertraline is 25 mg and 75 mg per dose. The pharmacologically effective dose for oxcarbazepine is 100 mg to 300 mg per dose. The preferred dosage range for oxcarbazepine is 150 mg to 300 mg per dose. The pharmacologically effective dose for guanfacine is 1 mg to 2.5 mg per dose. The preferred dosage range for guanfacine is 1.5 mg to 2 mg per dose.

The preferred dose ranges for each compound should be dosed together as a composition twice a day, once in the morning and once in the evening. The first dose should preferably be given at breakfast, preferably between 8:00 a.m. and 9:00 a.m. The second dose should preferably be given before dinner, preferably between 5:00 p.m. and 6:00 p.m.

Further a slow-release enteric coated formulation of each drug/compound used in the invention, i.e., for fluoxetine, sertraline, guanfacine and/or oxcarbazepine, would be expected to have the same combined effects in adolescents and adults with ASD needing pharmacologic treatment for aggression and/or paranoia. A pharmacologic hydrochloride salt or an ester of these compounds are generally how these drugs are manufactured and dosed.

A method of administering the novel three drug composition is also disclosed. The method of treating ASD in adolescents and adults exhibiting aggression and/or paranoia with social isolation includes administering the three-drug composition to the subject needing treatment, preferably in two doses. When administering the novel three drug composition in two doses, the first dose should preferably be given at breakfast, preferably between 8:00 a.m. and 9:00 a.m., and the second dose should preferably be given before dinner, preferably between 5:00 p.m. and 6:00 p.m.

Examples of treatment of adolescents and young adults with moderate to severe autism (ASD) exhibiting aggression and/or self-injury and paranoia with social isolation follow:

Example 1: 10-Year-Old Autistic Male

The following TABLE 1 provides the dosage quantities and frequency administered to a first exemplary patient:

TABLE 1

| COMPOUND | DOSE QUANTITY | DOSE FREQUENCY |
|---|---|---|
| Fluoxetine | 20 mg | Twice Daily: |
| Oxcarbazepine | 150 mg | Morning: 8:00 AM |
| Guanfacine | 1.5 mg | Evening: 5:30 PM |

For the first exemplary patient, a 10-year-old ASD male with language started on risperidone for self-injury and aggression toward others and paranoia—with social isolation behavior. The risperidone quickly (within 2 weeks) caused development of dyskinesia and dystonias where the patient could not sit still at all (literally was climbing the walls). The patient was taken off risperidone and 2 months later started on aripiprazole with successful alleviation of aggression and improvement in paranoia/social isolation behaviors. However, after 1 and ½ years on aripiprazole, the patient at age 11 and ½ developed tardive dyskinesia and dystonias and aripiprazole induced hallucinations, severe aggression and paranoia within a half hour of taking aripiprazole. The patient was taken off all medications and remained aggressive, self-injurious and paranoid. He was started on a regimen of fluoxetine and remained paranoid and unable to attend schooling, but his self-injury slightly decreased. Guanfacine and oxcarbazepine were then added to his regimen and after a few months the subject who was then age 12, 180 lbs and 5', 6", had his aggression and self-injurious behaviors markedly reduced and his paranoia was greatly relieved and he could attend school without any absences and had virtually no episodes of aggression at home or in public. His parent reported that the next year the dystonic and tardive dyskinesia virtually disappeared, while his aggression and paranoia remained greatly reduced and manageable with very few episodes of aggression or paranoia-social isolation behavior and no self-injury. The child continued to be able to attend school without absences. The adolescent has remained stable on the combination of these three medications for over two years.

Example 2: 15-Year-Old Autistic Male

The following TABLE 2 provides the dosage quantities and frequency administered to a second exemplary patient:

TABLE 2

| COMPOUND | DOSE QUANTITY | DOSE FREQUENCY |
|---|---|---|
| Sertraline | 25 mg | Together Twice Daily: |
| Oxcarbazepine | 200 mg | Morning: 8:00 AM |
| Guanfacine | 2 mg | Evening: 6:00 PM |

For the second exemplary patient, a 15-year-old ASD male, 6 feet, 280 lbs, who developed tardive dyskinesia on risperidone, and who exhibited aggression with injury to others and self and paranoia social isolation at home and in school, was successfully treated by replacing risperidone prescribed to treat aggression with a drug regimen having the above composition, given in the morning and evening.

Example 3: Adult Autistic Male in 20s

The following TABLE 3 provides the dosage quantities and frequency administered to a third exemplary patient:

TABLE 3

| COMPOUND | DOSE QUANTITY | DOSE FREQUENCY |
|---|---|---|
| Fluoxetine | 20 mg | Together Twice Daily: |
| Oxcarbazepine | 150 mg | Morning: Early Morning |
| Guanfacine | 2 mg | Evening: After 5:00 PM |

An adult male, in his twenties with ASD had a history of aggression with paranoia symptoms that had been treated with risperidone, but his self-injury behavior and aggression toward others could no longer be successfully treated with risperidone. Upon being treated with the combination 20 mg fluoxetine, 150 mg oxcarbazepine and 2 mg guanfacine, dosed early morning and after 5:00 pm, his aggression and symptoms of social isolation were alleviated and he became safer and more able to socially interact.

I claim:

1. A method of treating ASD adolescents and adults exhibiting aggression and/or paranoia with social isolation comprising:
    administering a three-drug composition comprising:
        a pharmacologically effective dose of a serotonin selective reuptake inhibitor;
        a pharmacologically effective dose of oxcarbazepine; and
        a pharmacologically effective dose of guanfacine;
        wherein the ASD adolescents and adults have been unsuccessfully treated with risperidone; wherein the serotonin selective reuptake inhibitor is selected from fluoxetine and sertraline.

2. The method of claim 1 wherein said pharmacologically effective doses of the serotonin selective reuptake inhibitor, oxcarbazepine, and guanfacine are administered as a pharmacologic hydrochloride salts and/or an ester of these compounds.

3. The method of claim 1 wherein the three-drug composition is administered in two doses, a first dose in the morning, and a second dose in the evening.

4. The method of claim 1 wherein said serotonin selective reuptake inhibitor is fluoxetine.

5. The method of claim 1 wherein said serotonin selective reuptake inhibitor is sertraline.

6. The method of claim 4 wherein said pharmacologically effective dose of fluoxetine is 10 mg to 30 mg.

7. The method of claim 5 wherein said pharmacologically effective dose of sertraline is 25 to 75 mg.

8. The method of claim 1 wherein said pharmacologically effective dose of oxcarbazepine is 100 mg to 300 mg.

9. The method of claim 1 wherein said pharmacologically effective dose of guanfacine is 1 mg to 2.5 mg.

10. A composition for treating autistic individuals comprising:
    a three-drug composition having a pharmacologically effective dose of a serotonin selective reuptake inhibitor, a pharmacologically effective dose of oxcarbazepine, and a pharmacologically effective dose of guanfacine;
    wherein the autistic individuals exhibit self-injury behavior and/or paranoia with social isolation; wherein the autistic individuals have been unsuccessfully treated with risperidone; wherein the serotonin selective reuptake inhibitor is selected from fluoxetine and sertraline.

11. The composition of claim 10, wherein said pharmacologically effective doses of the serotonin selective reuptake inhibitor, oxcarbazepine, and guanfacine are administered as hydrochloride salts or esters of these compounds.

12. The composition of claim 10, wherein said serotonin selective reuptake inhibitor is fluoxetine.

13. The composition of claim 10, wherein said serotonin selective reuptake inhibitor is sertraline.

14. The composition of claim 12 wherein said pharmacologically effective dose of fluoxetine is 10 mg to 30 mg.

15. The composition of claim 13 wherein said pharmacologically effective dose of sertraline is 25 mg to 75 mg.

16. The composition of claim 10 wherein said pharmacologically effective dose of oxcarbazepine is 100 mg to 300 mg.

17. The composition of claim 10 wherein said pharmacologically effective dose of guanfacine is 1 mg to 2.5 mg.

18. A composition for treating autistic individuals comprising:

a three-drug composition having a pharmacologically effective dose of a serotonin selective reuptake inhibitor, a pharmacologically effective dose of oxcarbazepine, and a pharmacologically effective dose of guanfacine;

wherein said pharmacologically effective dose of oxcarbazepine is 100 mg to 300 mg;

wherein said pharmacologically effective dose of guanfacine is 1 mg to 2.5 mg;

wherein the autistic individuals exhibit self-injury behavior and/or paranoia with social isolation; wherein the autistic individuals have been unsuccessfully treated with risperidone; wherein the serotonin selective reuptake inhibitor is selected from fluoxetine and sertraline.

* * * * *